United States Patent [19]

Sheryll

[11] Patent Number: 5,559,295

[45] Date of Patent: Sep. 24, 1996

[54] UNDERWATER SAMPLING METHOD AND APPARATUS

[76] Inventor: Richard P. Sheryll, 340 W. 87th St., New York, N.Y. 10024

[21] Appl. No.: 347,858

[22] Filed: Dec. 1, 1994

[51] Int. Cl.⁶ .................................................. G01N 1/12
[52] U.S. Cl. ............................. 73/864.63; 73/864.67
[58] Field of Search .......................... 73/864.61, 864.63, 73/864.65, 864.66, 864.67

[56] References Cited

U.S. PATENT DOCUMENTS

| | | | |
|---|---|---|---|
| 3,892,130 | 7/1975 | Winget et al. ................ | 73/864.62 |
| 4,037,477 | 7/1977 | Niskin ........................... | 73/864.67 |
| 4,593,570 | 6/1986 | Niskin ........................... | 73/864.67 |

*Primary Examiner*—Hezron E. Williams
*Assistant Examiner*—Nashmiya Ashraf
*Attorney, Agent, or Firm*—Cobrin Gittes & Samuel

[57] ABSTRACT

Underwater sampling apparatus for collecting uncontaminated samples from an underwater environment at in situ pressure includes a sample chamber in which the sample is to be collected, and a lid chamber in hydraulic or pneumatic communication with the sample chamber for defining a controllable interface between the sample chamber and the underwater environment. The lid chamber includes a stack of lid-chamber-defining plates coupled together to form a unitary whole and a lid movable between a closed position sealing the sample chamber and an open position in which the sample chamber is open to the undersea environment. Motion control element move the lid between the open and closed positions.

9 Claims, 7 Drawing Sheets

UNDERWATER SAMPLING METHOD AND APPARATUS

BACKGROUND OF THE INVENTION

This invention relates generally to a sampling device for use in an underwater environment, and, more particularly, relates to a modular, submersible device adapted for operation at abyssal depths, wherein operation includes collection of sedimentary, biological, or liquid undersea samples and recovery of such samples to the surface in an uncontaminated, unchanged form at abyssal pressure.

Underwater sampling of organisms, liquid, sediment, or geological formations has assumed increasing importance in recent years. In the area of pharmaceutical research, for example, numerous research programs have been promulgated with the objective of recovering, studying and utilizing deep-sea micro-organisms which synthesize agents having pharmaceutical benefit.

A wide array of devices have been developed for underwater sampling. Examples of such devices are set forth in the following United States and foreign patents:

| U.S. Pat. No. | Inventor |
| --- | --- |
| 1,702,060 | Scott |
| 1,994,847 | Baker |
| 1,994,848 | Baker et al. |
| 2,541,785 | Smith |
| 2,880,969 | Williams |
| 3,165,931 | Shipek |
| 3,225,602 | Barton |
| 3,302,464 | Langguth |
| 3,438,452 | Bernard et al. |
| 3,878,904 | Dobson |
| 3,892,130 | Winget et al. |
| 4,317,490 | Milberger et al. |
| 4,950,844 | Hallmark et al. |

| Patent No. | Country |
| --- | --- |
| 1268629 | Great Britain |
| 1400096 | Great Britain |
| 2184835 | Great Britain |
| 55-146023 | Japan |
| 1130690 | Soviet Union |
| 1555638 | Soviet Union |

For example, Milberger et al. (U.S. Pat. No. 4,317,490) relates to a sampling device in which a sample tube and ball valve are operated from the water surface via a drill string.

The Soviet patent (No. 1,555,638) shows a soil sampler for use with an underwater vehicle, in which the manipulator of the underwater vehicle controls movement of the sampler. Use of a tensioned flexible cord seals the sample.

Williams U.S. Pat. No. 2,880,969, Barton U.S. Pat. No. 3,225,602, Langguth U.S. Pat. No. 3,302,464 and Hallmark et al. U.S. Pat. No. 4,950,884 all disclose apparatus for collecting core samples. The Barton and Langguth patents are directed to samplers for collecting samples from underwater formations. The Williams patent is designed for coring formations that are non-flowing and open to the atmosphere.

Winget et al. U.S. Pat. No. 3,892,130 discloses a deep sea microbiological sampling and culturing apparatus and method.

Smith U.S. Pat. No. 2,541,785 shows a wellbore coring device which collects sample cores together with ambient fluid so that any fluid in the core may be brought to the surface within a core barrel.

British patent 1,400,096 and the Dobson U.S. Pat. No. 3,878,904 both disclose core samplers having a self-actuating closure or door at the bottom end of a sampling tube. Bernard et al. U.S. Pat. No. 3,438,452 discloses a deep sea core sampler for collecting sediment cores. British Patent No. 1,268,629 shows an underwater coring device utilizing a core barrel driven by a rotary member or actuator.

Similarly, British patent 2,184,835 discloses a core container for use in the storage of rock samples. Scott U.S. Pat. No. 1,702,060 shows a wellbore corer having a screw operated valve member to open and close a core chamber or barrel. Baker U.S. Pat. No. 1,994,847 and Baker et al. U.S. Pat. No. 1,994,848 both disclose rotary-driven core barrels.

Shipek U.S. Pat. No. 3,165,931 discloses a sea floor sediment sampler; the Japanese patent (55-146023) shows a non-mixing mud sampler and its sample tube; and Soviet patent 1,130,690A discloses a rock seam tester and sampler.

Underwater sampling devices typical of the prior art, however, suffer from a number of deficiencies. In particular, most sampling devices are designed for a single form of sampling, and lack versatility. Such devices are adequate for one type of sampling but are not appropriate for other forms of sampling. For example, devices typical of the prior art are adapted for sedimentary sampling, liquid sampling or biological sampling, but can not be employed for all three forms of sample recovery.

Certain conventional sampling devices, moreover, are not suitable for recovery of uncontaminated samples of plant or animal micro-organisms at in situ pressure.

Still further, many conventional underwater sampling devices can only obtain samples of a given, predetermined volume. Therefore, the researcher seeking a variety of sample volumes or sizes would need to deploy an assortment of different samplers. This entails increased cost and logistic burdens since the researcher will need to acquire, deploy and maintain various sampling devices having different sizes, purposes and mechanisms.

Accordingly, there exists a need for an improved apparatus and method for obtaining underwater samples from abyssal depths and for recovering such samples in an uncontaminated, unchanged form at in situ abyssal pressure.

It is therefore an object of the present invention to provide improved underwater sampling apparatus and methods.

It is another object of the invention to provide such apparatus that is versatile and which can be adapted for obtaining and recovering a wide variety of underwater samples, including biological, sedimentary and liquid samples.

It is a further object of the invention to provide such apparatus which is reliable, affords enhanced isolation of the sample and protection from contamination, and which is relatively simple and inexpensive to construct.

Other general and specific objects of the invention will in part be obvious and will in part appear hereinafter.

SUMMARY OF THE INVENTION

The foregoing objects are attained by the invention, one aspect of which relates to an underwater sampling method and apparatus for collecting uncontaminated samples from an underwater environment at in situ pressure. In one aspect of the invention, the apparatus includes a sample chamber in which the sample is to be collected, and a lid chamber coupled to the sample chamber in hydraulic or pneumatic communication therewith. The lid chamber includes lidchamber-defining elements and lid elements which cooperate to define a controllable interface between the sample chamber elements and the underwater environment.

In a further aspect of the invention, the lid chamber elements include movable lid elements for selectively sealing the sample chamber. The movable lid elements are movable between a first, closed position wherein the lid elements seal the sample chamber, and a second, open position wherein the sample chamber is open to the underwater environment.

The lid chamber elements can include a plurality of stacked lid-chamber-defining plates. The stacked lid-chamber-defining plates are coupled together by bolts or other fastening elements to form a unitary whole, and each of the stacked plates has a selected sectional configuration, for defining a lid-chamber through which the lid elements can move between the first, closed position and the second, open position.

Motion control elements, which can include one or more electric or hydraulic or pneumatic motors, are operatively connected to the lid elements for selectively moving the lid elements between the first, closed position, and the second, open position. The motion control elements and any associated electronic elements can be housed in an auxiliary chamber coupled to either the sample chamber or the lid chamber, and defined by auxiliary chamber elements.

In one aspect of the invention, the lid chamber elements are coupled to the sample chamber elements and the stacked lid-chamber-defining plates are coupled together by a set of bolts. Pressure sealing elements, such as O-rings or other known sealing elements, are interposed between each of the stacked lid-chamber-defining plates to prevent leakage therebetween. The invention can also utilize coring tubes to obtain a core sample if such is desired. The coring tube can be attached to the outermost or lowermost lid-chamber defining plate.

In another aspect of the invention, elements are provided for pumping snubbing fluid into the sample chamber and/or the lid chamber to displace air or other fluid during operation and to prevent collapse of the chambers prior to pressure equalization at abyssal depths. In addition, a bladder element can be provided to dispense a cleansing solution when the lid element closes, to wash contaminants from the lid and thereby reduce or prevent contamination of the lid seals during closure.

In a further aspect of the invention, one or more valves and/or ports can be provided in fluid communication and/or electronic communication with the sample chamber and/or the lid chamber. The electronic communication can be employed to permit manipulation of a sample within the chamber, i.e., by connection to a motor, a temperature gauge, or other sensors or motive devices. These valves and ports can also enable selected removal of a portion of the sample upon recovery, for example by use of a syringe or like elements. The ports can further be used for pressurizing the vessel; for controlled de-pressurization; for pressure equalization of the sampler chamber and lid chamber; and as "windows" or viewports.

The invention can be utilized in conjunction with a manipulator elements (e.g. mechanical arm) either within the sample chamber or within an auxiliary chamber, for obtaining rock samples or biological samples. In addition, the device can be utilized for obtaining water samples, or as an instrumentation platform.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF ILLUSTRATED EMBODIMENTS

Figure 1:
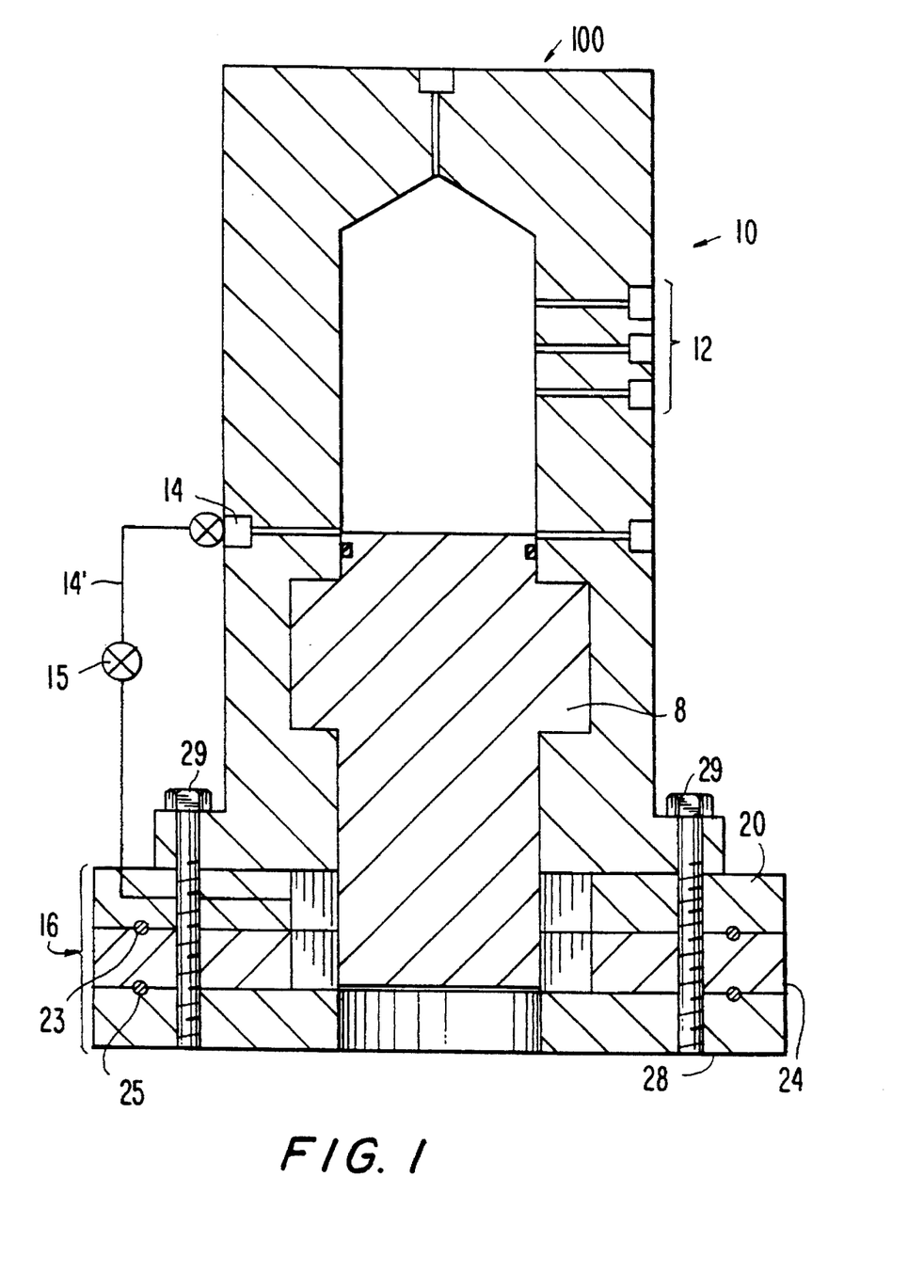
FIG. 1 is a simplified, cross-sectional side view of one embodiment of an underwater sampling apparatus in accordance with the invention, showing the relative positions of sample chamber, lid chamber and movable lid element.

FIG. I is a simplified sectional view of one embodiment of an underwater sampling apparatus in accordance with the invention for collecting uncontaminated samples from an underwater environment at in situ pressure. The apparatus includes a sample chamber in which the sample is to be contained, and a lid chamber (only a portion of which is shown in FIG. 1) coupled to the sample chamber in hydraulic or pneumatic communication therewith. The lid chamber includes lid-chamber-defining elements which define a controllable interface between the sample chamber and the underwater environment. The lid chamber elements include movable lid elements for selectively sealing the sample chamber. The movable lid elements are movable between a first, closed position wherein the lid elements seal the sample chamber, and a second, open position wherein the sample chamber is open to the underwater environment.

The lid chamber elements can include a plurality of stacked lid-chamber-defining plates. The stacked lid-chamber-defining plates are coupled together by bolts or other fastening elements to form a unitary whole, and each of the stacked plates has a selected sectional configuration, for defining a lid-chamber through which the lid elements can move between the first, closed position and the second, open position.

The use of stacked plates provides significant advantages over the use of a solid, one-piece chamber. The stacked plate design reduces the cost of the device, and allows the user to change internal function by changing the plate design to adapt to different sampling tasks, a feature which is not possible for a one-piece chamber design.

Motion control elements, which can include one or more electric, hydraulic or pneumatic motors, are operatively connected to the lid elements for selectively moving the lid elements between the first, closed position, and the second, open position.

In particular, FIG. 1 is a simplified cross sectional side view of one embodiment of an underwater sampling apparatus 100 according to the invention, including: sample chamber 10, having sample chamber ports 12, pressure equalization port 14 and conduit system 14', valve 15, lid 8 and lid chamber 16, including a first layer formed from lid-chamber-defining plate 20, a second layer formed from lid-chamber-defining plate 24, a third layer formed from lid-chamber-defining plate 28, and attachment bolts 29 for selectively attaching modules such as sample chamber 10. O-rings 23 and 25 provide sealing between the plates.

Figure 4A:
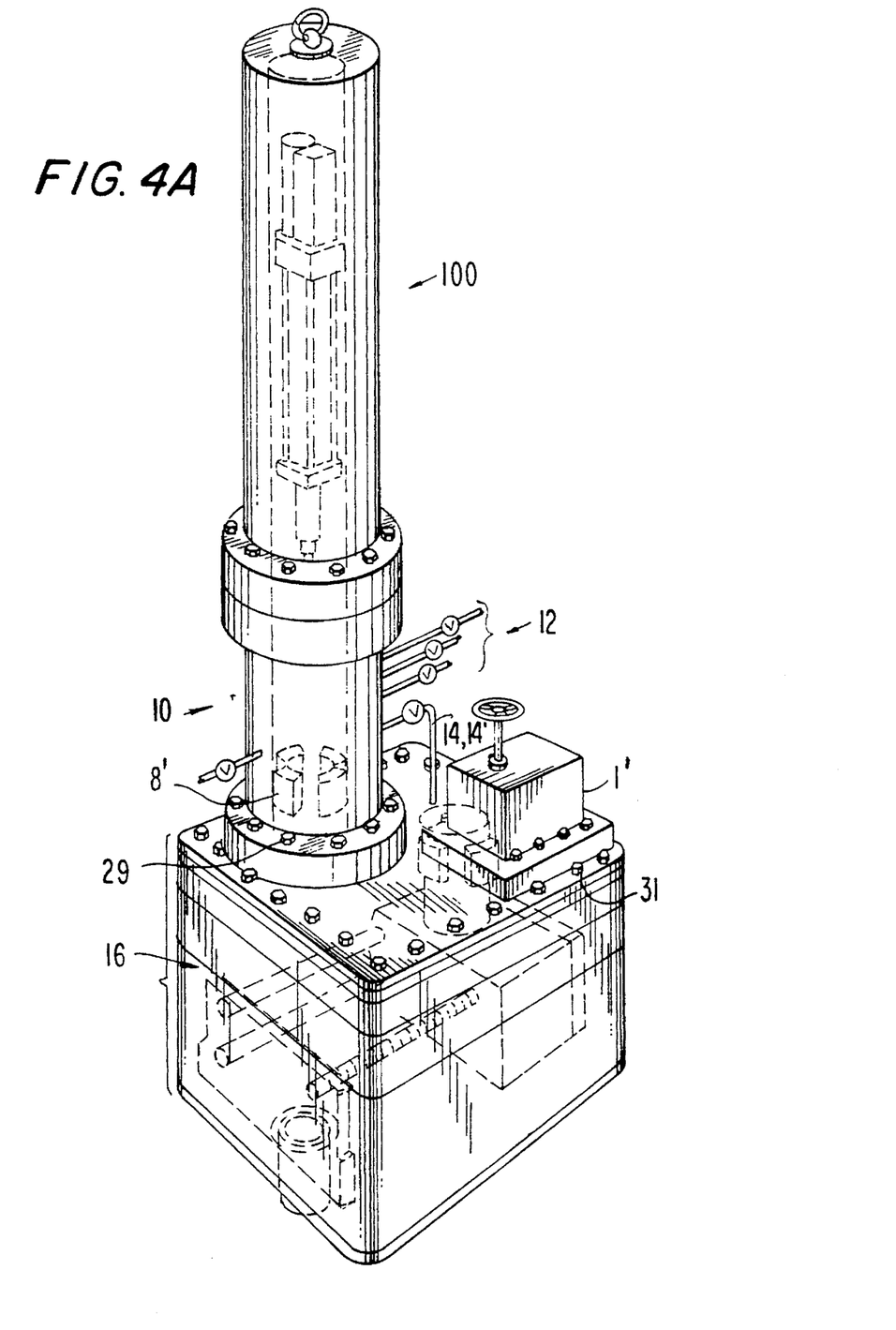
FIGS. 4A and 4B are three-quarter and side views, respectively, depicting another embodiment of the invention, showing movable elements of the sampling apparatus in phantom.
Figure 4B:
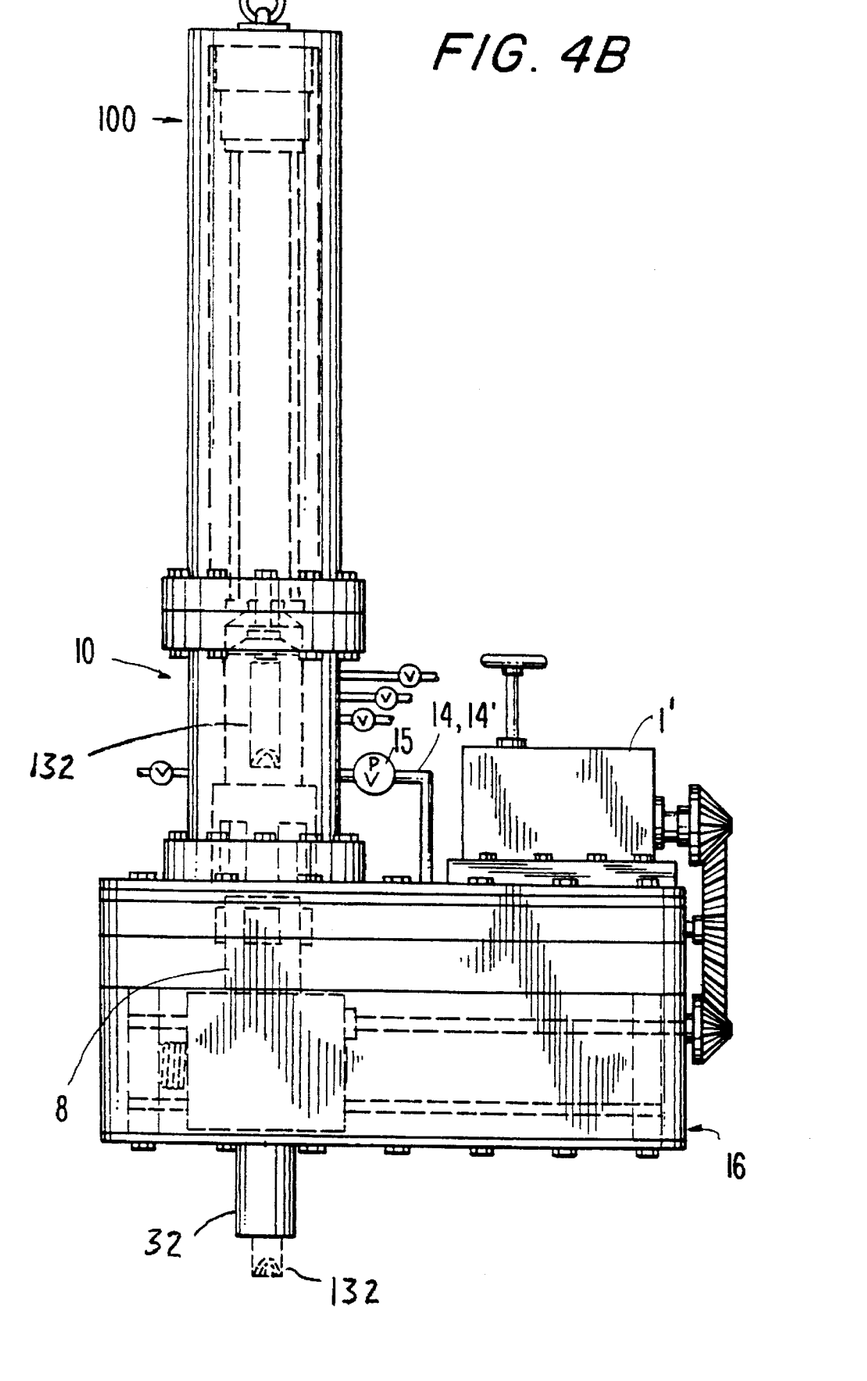
Figure 5:
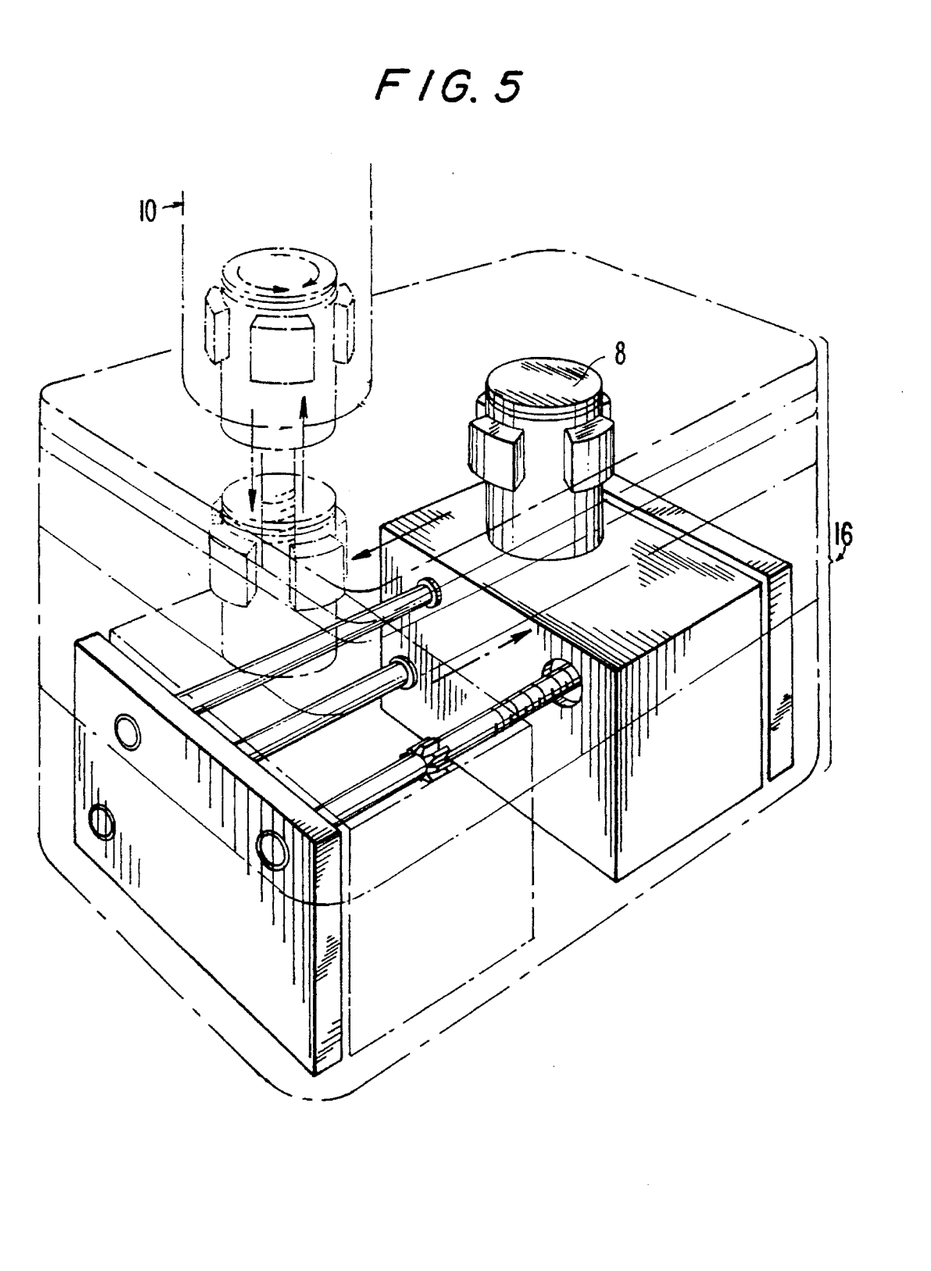
FIG. 5 shows the movement of the lid element of FIGS. 4A and 4B within the lid chamber thereof.

FIGS. 4A and 4B are perspective and side views, respectively, depict another embodiment of the invention, showing movable elements of the sampling apparatus in phantom;

In the embodiment illustrated in FIGS. 1, 4A and 4B the apparatus is modular and requires at least two modules to operate: lid chamber 16 and sample chamber 10. The sample chamber 10 is coupled to the lid chamber 16 by the attachment bolts or similar fixtures 29 (FIGS. 4A, 4B). However, as will be apparent to those skilled in the art, auxiliary chambers may be attached to the sample chamber 10 for housing motion control elements such as hydraulic or electrical motors or actuators, and associated electronics, as required by particular applications.

The lid chamber 16 depicted in FIGS. 1, 4A and 4B functions as an interface between the sample chamber 10 and an outside environment. In the embodiment depicted therein, the lid chamber 16 is a module having layers of lid-chamber-defining plates, which may be stainless steel or other suitable material resistant to corrosive attack by seawater, coupled together in a hermetically sealed formation utilizing O-rings 23, 25 (FIG. 1) or other seals. These layers house the lid 8 when the module is in the open position and also contain motion control elements which drive the lid 8 between the open position and a closed position.

Figure 2:
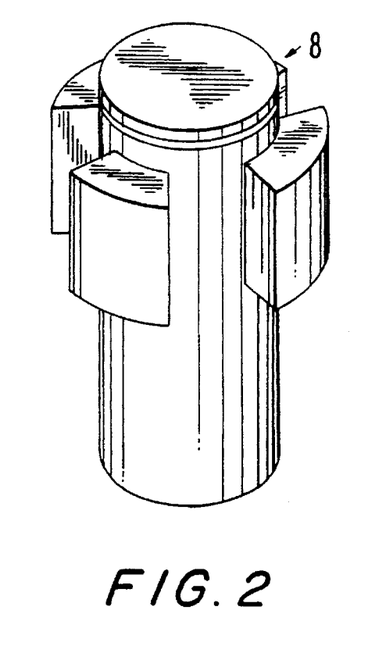
FIG. 2 depicts the movable lid element of the apparatus of FIG. 1.
Figure 3A:
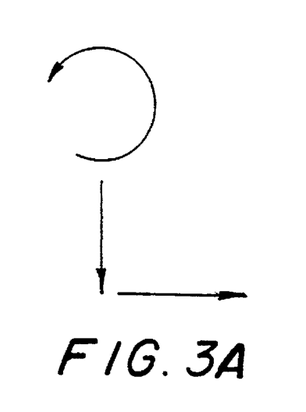
FIGS. 3A and 3B depict the rotational, vertical and horizontal movement of the movable lid element of the underwater sampling apparatus of FIG. 1.
Figure 3B:
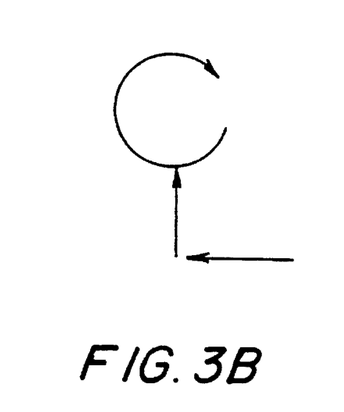

The shape of the lid 8 in one embodiment of the invention is shown in FIG. 2. In simplified form, the movement of the lid 8 during operation is depicted in the FIGS. 3A and 3B. As shown therein, when the lid is to be moved to the open position, it is first rotated forty-five degrees (FIG. 3A), then dropped down through the lid chamber, and then translates horizontally along the lid chamber, thereby permitting fluid, sediment, or other desired sample volumes to pass through the lid chamber. Other movements can be utilized, such as an arcuate movement. When the lid 8 is to be moved to the closed position, then the lid 8 translates horizontally across the lid chamber defining plates, then moves upward, and finally is rotated 45 degrees to seal with internal sealing elements 8' (FIG. 4a) of the sample chamber.

Figure 6:
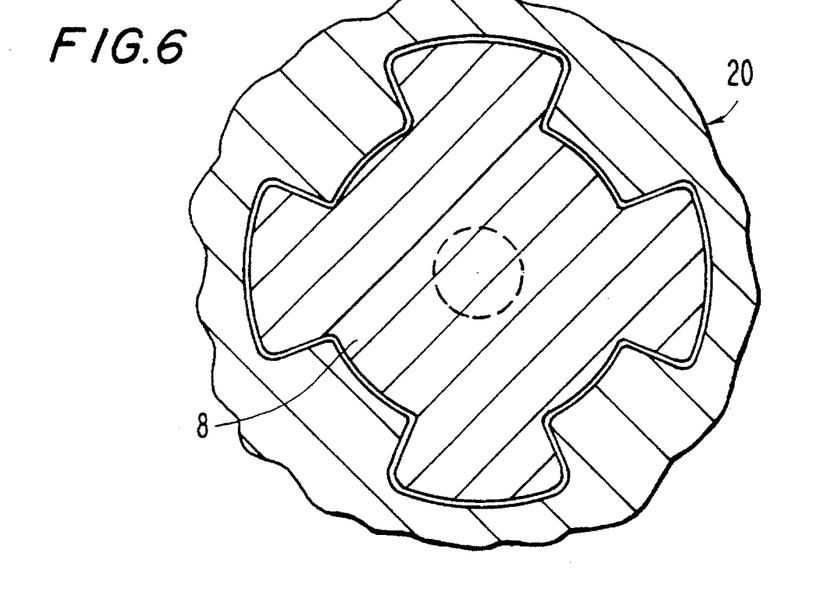
FIGS. 6 and 7 show the movable lid element in locked and unlocked positions within the chamber respectively.
Figure 7:
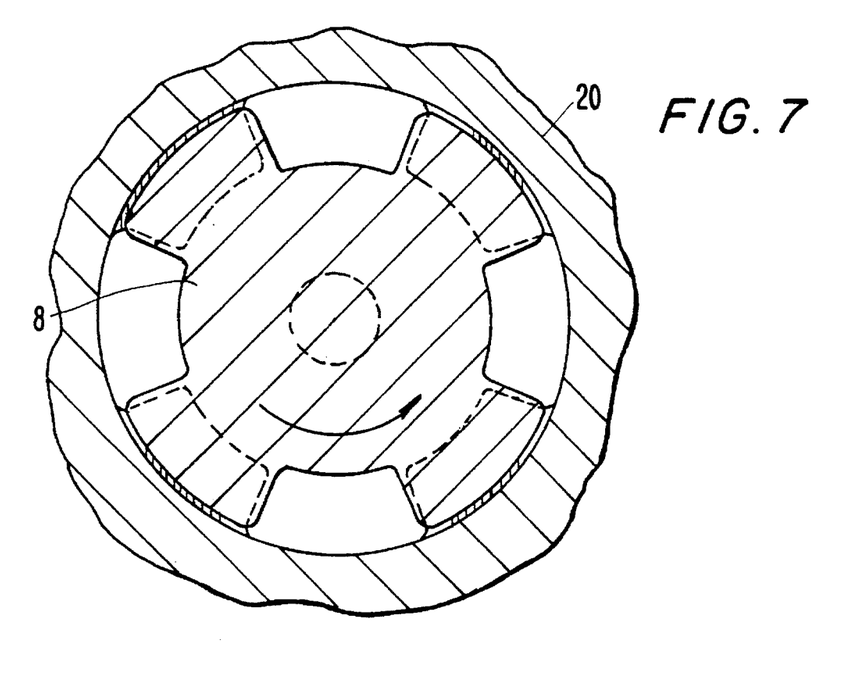
Figure 8:
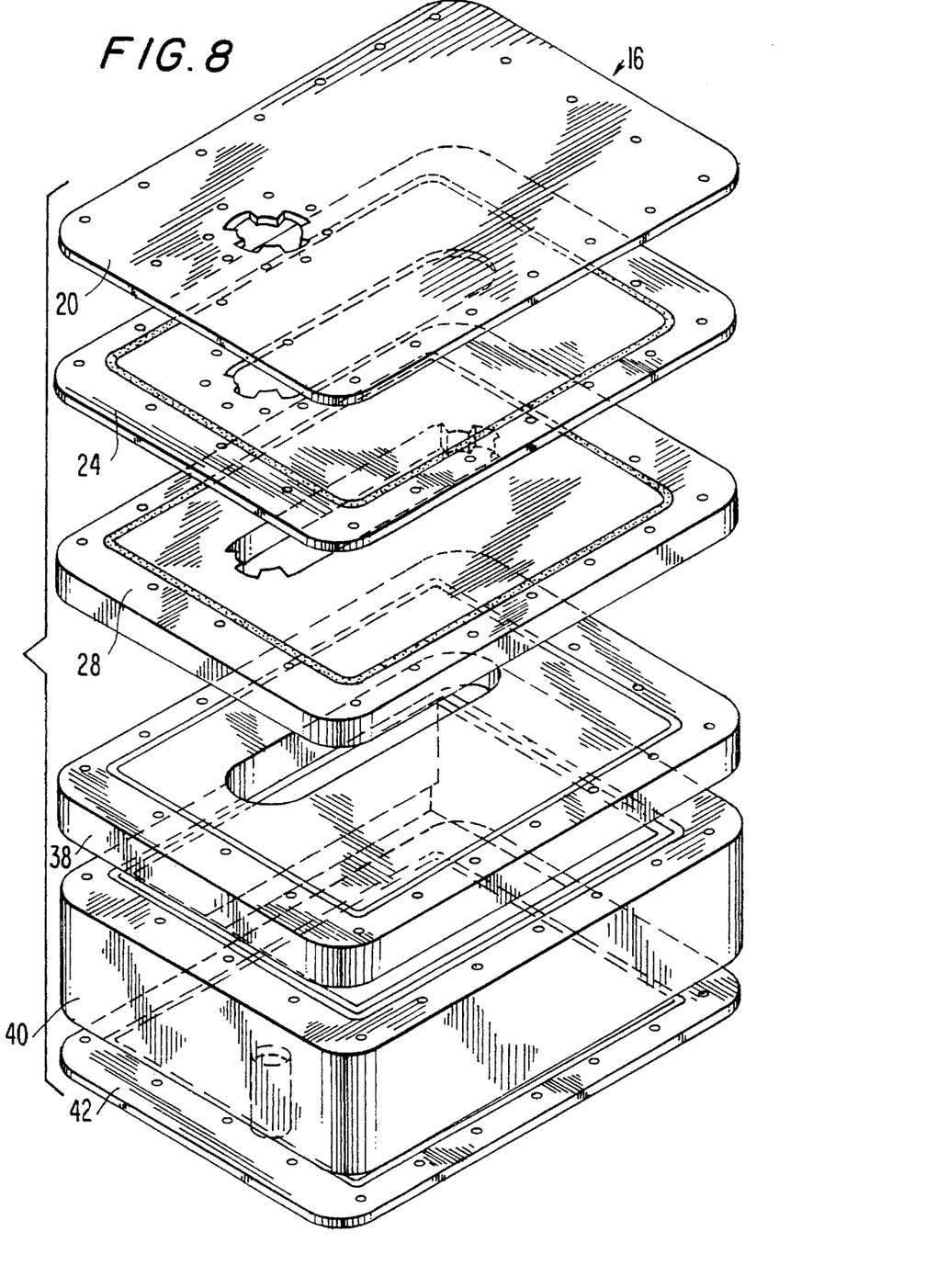
FIG. 8 depicts the lid-chamber-defining plates of the embodiment of FIGS. 4A and 4B.

Similarly, FIGS. 5–8 depict movement of the lid 8 from the sample chamber to the lid chamber 16. In particular, the specially slotted configuration of lid-defining-plates 20, 24, 28, 38, 40 and 42 are shown in FIG. 8. FIG. 6 shows the lid in the unlocked position, while FIG. 7 shows the lid in the locked position.

As shown in the accompanying drawings, particularly FIGS. 1, 4A and 4B, the uppermost lid-chamber-defining element is in contact with the sample chamber 10. The lowermost lid-chamber-defining element can be placed in contact with a conventional coring tube. The lid chamber 16 can be implemented in a variety of different configurations other than those shown in FIGS. 1, 4A and 4B, dependent upon the desired application. For example, if a sample to be retrieved, such as a core sample for a bacteriological study, is to be maintained in a gaseous atmosphere, then the lid-chamber-defining plate in contact with the lowermost plate may be fitted with a coring tube 32 (FIG. 4B) which can contain a tube cap which is removed during pressure equalization. In particular, the coring tube 32 can be capped by a tube cap (not shown) which maintains uncomtaminated the distal end of the coring tube 32 and the lid chamber, and which can retain a snubbing fluid within the coring tube 32 and lid chamber 16, as will next be described.

The device can be suspended from a framework or held by a mechanical arm from an underwater vehicle, or can be fitted with a flotation collar to maintain the device in an upright position.

In operation, as the device is lowered through the abyssal depths, steps must be taken to prevent the device from imploding under the immense ambient pressure. Accordingly, the sample chamber is filled with gas to a selected pressure greater than that of the desired sampling depth. The selected pressure takes into account the volume needed to displace a snubbing fluid from the lid chamber, as will next be described, as well as the pressure of the desired sampling depth.

Next, the lid chamber 16 is filled with an incompressible snubbing fluid. This fluid completely fills the lid chamber 16 and the coring tube 32 and conduit 14' leading to sample chamber 10. The extremely high ambient pressure is balanced by the snubbing fluid pumped into the lid chamber 16 and the coring tube 32 and conduit 14'. This prevents the lid chamber 16 from collapsing.

When the apparatus reaches its sampling depth a drive device, such as an onboard electrical, hydraulic or pneumatic motor or actuator, or the movable arm of a submersible submarine device, opens valve 15, thereby releasing the high pressure gas from the sample chamber 10 into the lid chamber 16. As this gas enters the lid chamber 16 it displaces the snubbing fluid, dislodges the tube cap from the end of the coring tube 32, and forces the snubbing fluid out of the lid chamber 16. Thus, in order to accomplish pressure equalization, the high pressure gas from the sample chamber is released into the lid chamber through equalization conduit system 14' and valve 15, expelling the snubbing fluid from the lid chamber 16. Accordingly, during pressure equalization the snubbing fluid is displaced by gas from the sample chamber 10, which then fills the lid chamber 16 until the pressure in lid chamber 16, sample chamber 10 and the external pressure are all equal.

When the internal pressure has equalized with the external pressure, the driver device, which can also include a gear train, or a number of independent electrical, hydraulic or pneumatic motors or actuators, opens the lid chamber 16.

The driver devices and/or motion control elements turn the lid 8 forty-five degrees (see FIGS. 3A, 3B, 5, 6 and 7), then propel the lid downward until it is clear of the sample chamber 10. (See FIG. 5.) The motion control elements then propel the lid to one side of the opening or entrance to the sample chamber 10. Once the lid 8 is clear, the motion control elements stop moving the lid element and actuate a further drive element, which in one embodiment of the invention can be a linear displacement transducer (LVDT) or similar actuator located inside the sample chamber 10 or the auxiliary chamber (reference numeral 1, FIGS. 4A and 4B), and which holds a piston and core catcher within a coring tube liner 132. The LVDT moves this liner 132 through the sample chamber 10, through the lid chamber 16, and into the coring tube 32 where it is placed for sample collection.

When used as a core sampler, the apparatus is then pushed into the bottom sediment by action of an external force such as that provided by a submersible vessel. This action pushes the piston in the coring tube liner which actuates the linear displacement transducer to pull the sample into the sample chamber 10.

Alternatively, when in a framework configuration a gravity deployment scheme can be employed in which the cable holding the sampler is lengthened and the sampler is dropped into the sediment. Specifically, at the sample site the device is lowered to within a few meters above the sediment, then allowed to equalize its internal sample chamber pressure to that of the external environment via the lid chamber. When equilibrium is attained, the device is allowed to free-fall to the ocean bottom. The mass of the system and its downward momentum will bury the core tube in the sediment, thereby taking a core sample.

In one embodiment of the invention, during retrieval of the sample into the lid chamber, the coring tube liner 132 passes through the lid chamber 16, and actuates a further drive element which places a tube cap on the bottom of the coring tube liner 132 as it is pulled through the lid chamber 16. This tube cap prevents the sample or associated sediments from escaping out of the coring tube liner 132.

In one embodiment of the invention, when the sample is fully retracted into the sample chamber 10, distilled water is sprayed over the entrance to the sample chamber 10, and the drive device is actuated to close the lid 8 on the sample chamber 10. The lid 8 closes into place, the equalization valve 15 is closed, and the sampler device is then brought to the surface. The distilled water may be stored in a breakable bladder element, which is ruptured when the sample is fully retracted into the sample chamber.

Once on the surface, the sample chamber 10 is removed from the lid chamber 16 by removal of bolts 29. The lid chamber 16 is then fitted with a new sample chamber 10 and the sample chamber 10 containing the sample can be then taken to a laboratory for analysis, such as by extraction or inspection through ports 12. This represents a significant advantage and improvement over the art, which is made possible by the modular nature of the apparatus.

While the foregoing description of operation pertains generally to obtaining of core samples or sediment samples, those skilled in the art will recognize that the apparatus can be utilized in a similar manner to obtain fluid samples or biological samples.

Those skilled in the art will also recognize that a wide variety of driving devices can be utilized, including one or more electrical, hydraulic or pneumatic motors, actuators or LVDTs.

In addition, the sample chamber can be fitted with a carousel or other multiple-site deployment device, whereby multiple, separate samples can be obtained from a given site or from different sites. Moreover, the device can be suitably adapted for the performance of on-board analysis or experiments on the samples obtained, with telemetry of results to the surface.

It will thus be seen that the invention efficiently attains the objects set forth above, among those made apparent from the preceding description. In particular, the invention provides a versatile and reliable apparatus for obtaining fluid, biological, or sediment samples at abyssal depths, and for recovering such samples in an unchanged, uncontaminated form at in situ pressure.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense. It is also to be understood that the following claims are intended to cover all of the generic and specific features of the invention as described herein, and all statements of the scope of the invention which, as a matter of language, might be said to fall therebetween. Having described the invention, what is claimed as new and secured by Letters Patent is:

What is claimed is:

1. Underwater sampling apparatus for collecting uncontaminated samples from an underwater environment at in situ pressure, said apparatus comprising a sample chamber in which a sample is to be collected, said sample chamber having an opening, and a lid chamber coupled to said sample chamber and defining a controllable interface between said sample chamber and the underwater environment, said lid chamber including a movable lid movable between a closed position wherein said lid closes said opening to seal said sample chamber, and an open position wherein said lid is clear of said opening and said sample chamber is open to the underwater environment, and a plurality of stacked lid-chamber-defining plates, said stacked lid-chamber-defining plates being coupled together to form a unitary whole, each of said stacked plates having a respective aperture, each said respective aperture being aligned with each other to define lid-chamber through which said lid is movable between said closed position and said open position such that said lid at said open position is spaced from said lid at said closed position, and motion control elements which selectively move said lid between said closed position and said open position.

2. Apparatus according to claim 1, further comprising.

an auxiliary chamber, coupled to any of said sample chamber and said lid chamber, for containing any of said motion control elements or electronic elements.

3. Apparatus according to claim 1, wherein said lid chamber is coupled to said sample chamber by a first set of bolts, and wherein said stacked lid-chamber-defining plates are coupled together by a second set of bolts, with pressure sealing elements interposed between said stacked lid-chamber-defining plates.

4. Apparatus according to claim 1, further comprising pressure equalization elements, including elements for delivering pressurized fluid or gas to any one of the sample chamber and the lid chamber, to balance with ambient abyssal pressure.

5. Apparatus according to claim 4, wherein said pressure equalization elements include a conduit and valve providing selective fluid communication between said sample chamber and said lid chamber.

6. Apparatus as in claim 1, wherein said respective apertures each define a configuration that differs from each other.

7. Apparatus according to claim 1 wherein said lid chamber is in electronic communication with any one of said sample chamber and said auxiliary chamber.

8. Apparatus according to claim 1, further comprising an incompressible snubbing fluid within said lid chamber.

9. Apparatus according to claim 8, further comprising pressure equalization elements, including elements for delivering pressurized fluid or gas to at least one of the sample chamber and the lid chamber, to displace the incompressible snubbing fluid and balance with ambient abyssal pressure.

\* \* \* \* \*